United States Patent
Honda

(10) Patent No.: US 9,877,694 B2
(45) Date of Patent: Jan. 30, 2018

(54) X-RAY COMPUTED TOMOGRAPHY APPARATUS AND X-RAY GENERATION APPARATUS

(71) Applicant: Toshiba Medical Systems Corporation, Otawara-shi (JP)

(72) Inventor: Toyomasa Honda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 214 days.

(21) Appl. No.: 14/746,191

(22) Filed: Jun. 22, 2015

(65) Prior Publication Data
US 2015/0289352 A1 Oct. 8, 2015

Related U.S. Application Data

(63) Continuation of application No. PCT/JP2014/050366, filed on Jan. 10, 2014.

(30) Foreign Application Priority Data

Jan. 10, 2013 (JP) ................................ 2013-002893
Jan. 10, 2014 (JP) ................................ 2014-003523

(51) Int. Cl.
*A61B 6/03* (2006.01)
*H05G 1/08* (2006.01)
(Continued)

(52) U.S. Cl.
CPC ............... *A61B 6/542* (2013.01); *A61B 6/03* (2013.01); *A61B 6/032* (2013.01); *A61B 6/40* (2013.01);
(Continued)

(58) Field of Classification Search
CPC ......... A61B 6/032; A61B 6/40; A61B 6/4435; A61B 6/54; A61B 6/542; H05G 1/04;
(Continued)

(56) References Cited

U.S. PATENT DOCUMENTS 4,601,051 A * 7/1986 Santurtun ............... H05G 1/54
378/105
4,654,770 A * 3/1987 Santurtun ............... H05G 1/54
361/93.9
(Continued)

FOREIGN PATENT DOCUMENTS

JP H03-210799 A 9/1991
JP H03-285299 A 12/1991
(Continued)

OTHER PUBLICATIONS

International Search Report issued Feb. 10, 2014 for PCT/JP2014/050366 dated Jan. 10, 2014 with English Translation.
(Continued)

*Primary Examiner* — Allen C. Ho
(74) *Attorney, Agent, or Firm* — Oblon, McClelland, Maier & Neustadt, L.L.P.

(57) ABSTRACT

According to on embodiment, an inverter high voltage generator includes a DC power supply, an inverter, a high voltage converter, a discharge detector, a controller. The DC power supply generates a direct current. The inverter converts the direct current from the DC power supply to an alternating current by switching. The high voltage converter converts an AC output pulse from the inverter to a high voltage. The discharge detector detects an electric discharge that has occurred in an X-ray tube. The controller controls, upon detection of the discharge, switching of the inverter to change a pulse width or a frequency of the AC output pulse from the inverter so as to gradually increase a measured tube voltage value of the X-ray tube up to a target tube voltage value.

8 Claims, 6 Drawing Sheets

(51) Int. Cl.
*H05G 1/10* (2006.01)
*H05G 1/12* (2006.01)
*H05G 1/26* (2006.01)
*H05G 1/30* (2006.01)
*H05G 1/32* (2006.01)
*H05G 1/34* (2006.01)
*H05G 1/54* (2006.01)
*A61B 6/00* (2006.01)
*H05G 1/04* (2006.01)
*H05G 1/22* (2006.01)
*G01N 23/04* (2006.01)
*G06T 11/00* (2006.01)
*H05G 1/56* (2006.01)
*H05G 1/46* (2006.01)

(52) U.S. Cl.
CPC .............. *A61B 6/4435* (2013.01); *A61B 6/54* (2013.01); *G01N 23/046* (2013.01); *G06T 11/003* (2013.01); *H05G 1/04* (2013.01); *H05G 1/08* (2013.01); *H05G 1/10* (2013.01); *H05G 1/12* (2013.01); *H05G 1/22* (2013.01); *H05G 1/26* (2013.01); *H05G 1/265* (2013.01); *H05G 1/30* (2013.01); *H05G 1/32* (2013.01); *H05G 1/34* (2013.01); *H05G 1/46* (2013.01); *H05G 1/54* (2013.01); *H05G 1/56* (2013.01); *G01N 2223/304* (2013.01); *G01N 2223/419* (2013.01); *G06T 2207/10072* (2013.01); *G06T 2207/10116* (2013.01)

(58) Field of Classification Search
CPC .. H05G 1/08; H05G 1/10; H05G 1/12; H05G 1/26; H05G 1/265; H05G 1/30; H05G 1/32; H05G 1/34; H05G 1/54
USPC ... 378/91, 101, 104, 106, 107, 117, 118, 16, 378/111, 112
See application file for complete search history.

(56) References Cited

U.S. PATENT DOCUMENTS

| | | | | |
|---|---|---|---|---|
| 4,661,896 A * | 4/1987 | Kobayashi | ............... | H05G 1/20 323/266 |
| 4,741,010 A * | 4/1988 | Hino | ............... | H05G 1/32 363/17 |
| 4,794,506 A * | 12/1988 | Hino | ............... | H02M 3/3376 363/132 |
| 4,928,295 A * | 5/1990 | Tanaka | ............... | H05G 1/32 378/104 |
| 5,187,737 A * | 2/1993 | Watanabe | ............... | H05G 1/08 363/17 |
| 5,339,348 A * | 8/1994 | Wirth | ............... | H05G 1/66 378/91 |
| 5,400,385 A * | 3/1995 | Blake | ............... | H05G 1/32 323/280 |
| 5,602,897 A * | 2/1997 | Kociecki | ............... | H05G 1/06 378/101 |
| 6,563,717 B2 * | 5/2003 | Lunding | ............... | H02M 3/285 363/15 |
| 6,738,275 B1 * | 5/2004 | Beland | ............... | H02M 1/088 363/21.02 |
| 7,050,539 B2 * | 5/2006 | Loef | ............... | H02M 3/285 363/15 |
| 7,305,065 B2 * | 12/2007 | Takahashi | ............... | H05G 1/12 378/101 |
| 7,315,462 B2 * | 1/2008 | Melhem | ............... | H02M 1/38 363/131 |
| 7,327,827 B2 * | 2/2008 | Sakamoto | ............... | H05G 1/12 378/101 |
| 7,400,708 B2 * | 7/2008 | Takahashi | ............... | H05G 1/10 378/101 |
| 7,830,685 B2 * | 11/2010 | Wagner | ............... | H02M 3/285 363/17 |
| 7,924,981 B2 * | 4/2011 | Iijima | ............... | H05G 1/12 378/110 |
| 8,385,504 B2 * | 2/2013 | Hattrup | ............... | H02M 1/40 378/101 |
| 8,588,371 B2 * | 11/2013 | Ogawa | ............... | H02M 7/53871 378/101 |
| 8,861,681 B2 * | 10/2014 | Caiafa | ............... | H02M 3/337 378/101 |
| 8,983,026 B2 * | 3/2015 | Ishiyama | ............... | A61B 6/035 378/105 |
| 9,036,784 B2 * | 5/2015 | Oketa | ............... | H02H 7/122 378/109 |
| 9,438,120 B2 * | 9/2016 | Caiafa | ............... | H02M 3/33507 |

FOREIGN PATENT DOCUMENTS

| | | |
|---|---|---|
| JP | H04-111310 U | 9/1992 |
| JP | H09-115685 A | 5/1997 |
| JP | H10-106792 A | 4/1998 |
| JP | 2002-306469 A | 10/2002 |
| JP | 2003-116841 A | 4/2003 |
| JP | 2005-192799 A | 7/2005 |
| JP | 2007-220514 A | 8/2007 |
| JP | 2011-176927 A | 9/2011 |

OTHER PUBLICATIONS

Written Opinion issued Feb. 10, 2014 for PCT/JP2014/050366 dated Jan. 10, 2014.

* cited by examiner

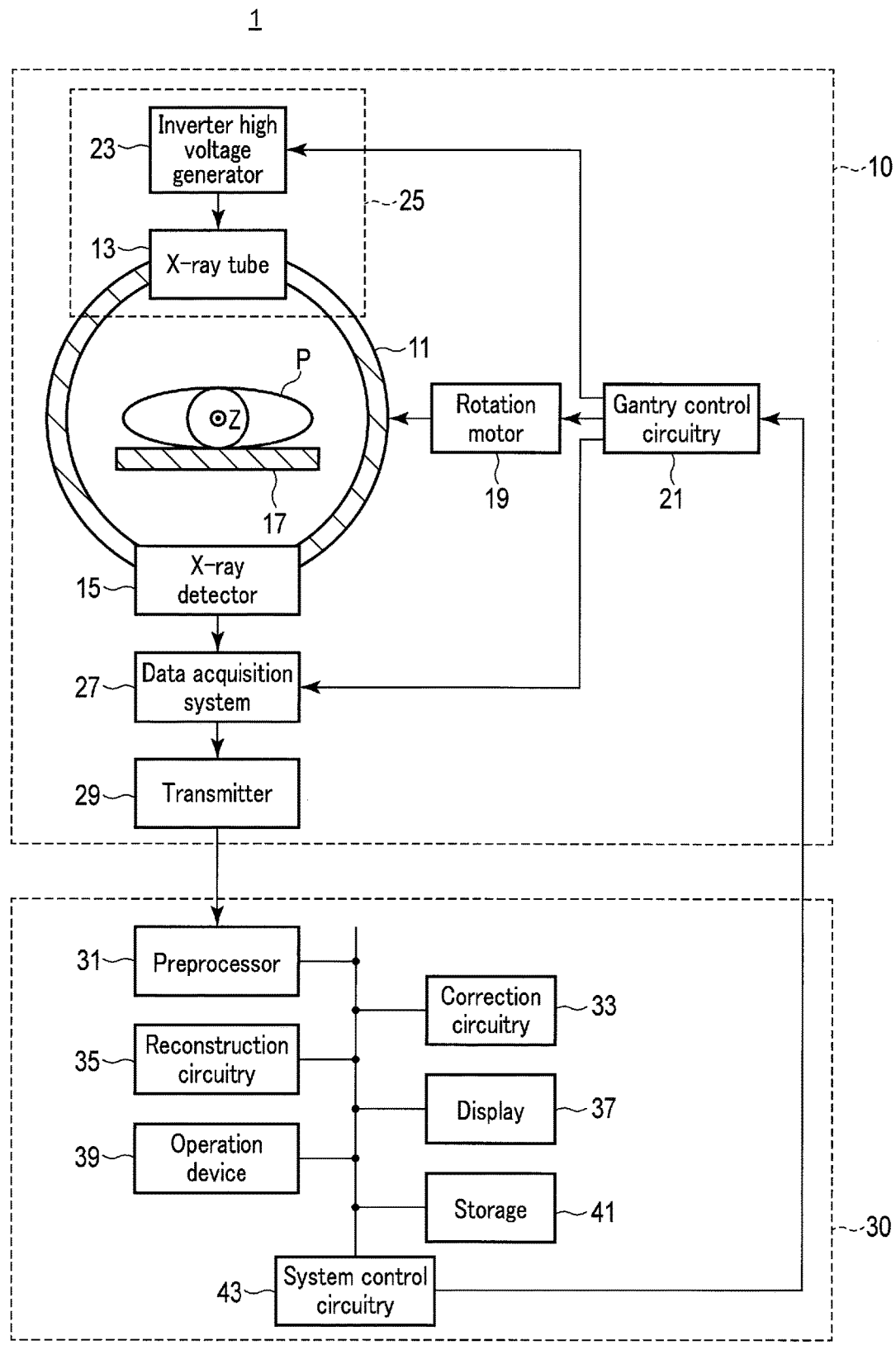
F I G. 1

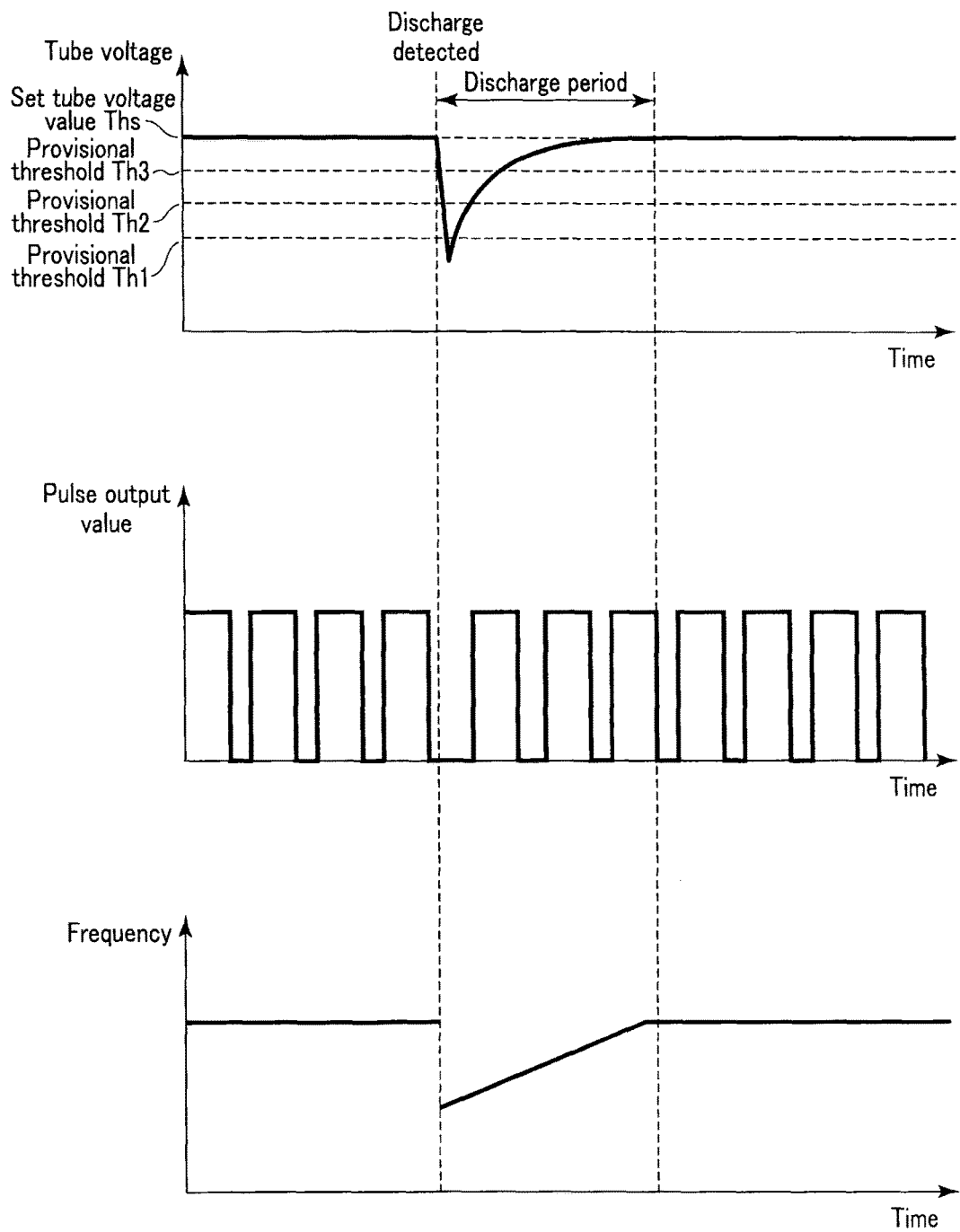
F I G. 4

X-RAY COMPUTED TOMOGRAPHY APPARATUS AND X-RAY GENERATION APPARATUS

CROSS-REFERENCE TO RELATED APPLICATIONS

This application is a Continuation application of PCT Application No. PCT/JP2014/050366, filed Jan. 10, 2014 and based upon and claims the benefit of priority from the Japanese Patent Application No. 2013-002893, filed Jan. 10, 2013, and No. 2014-003523, filed Jan. 10, 2014, the entire contents of all of which are incorporated herein by reference.

FIELD

Embodiments described herein relate generally to an X-ray computed tomography apparatus and an X-ray generation apparatus.

BACKGROUND

An electrical discharge (hereinafter "discharge") may occur in an X-ray tube. If a discharge occurs in an X-ray tube, a power supply to the X-ray tube is immediately shut off to stop X-ray emission. After the atmosphere within the x-ray tube becomes stable, the power supply to the X-ray tube is resumed to restart X-ray emission. The period of stopping X-ray emission by shutting off the power supply to the X-ray tube after a discharge has occurred is from several tens of milliseconds to several hundred milliseconds. During the period of stopping emission, data used to reconstruct an image cannot be acquired, thereby artifacts generate in a reconstructed image. Accordingly, the occurrence of an electrical discharge interferes with diagnosis.

BRIEF DESCRIPTION OF THE DRAWING

FIG. 1 illustrates a configuration of an X-ray computed tomography apparatus according to the present embodiment.

FIG. 4 illustrates an example timing chart of an operation of a frequency modulation system performed by the X-ray generation apparatus shown in FIG. 2.

DETAILED DESCRIPTION

Figure 2:
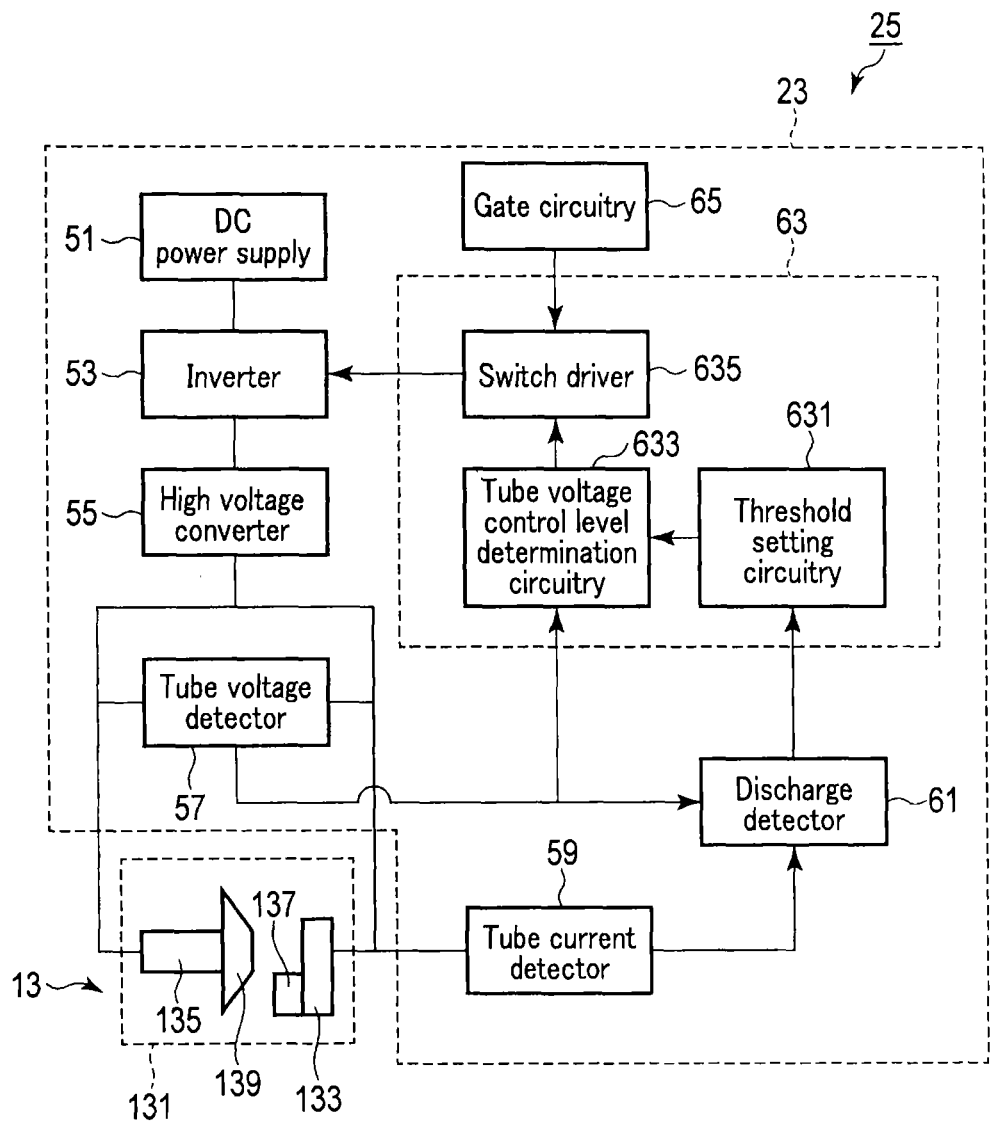
FIG. 2 illustrates a configuration of an X-ray generation apparatus shown in FIG. 1.

In general, according to one embodiment, an X-ray computed tomography apparatus includes an X-ray tube, an inverter high voltage generator, an X-ray detector, a supporting mechanism, a reconstruction circuitry. The X-ray tube is configured to generate X-rays. The inverter high voltage generator is configured to generate a high voltage to be applied to the X-ray tube. The X-ray detector is configured to detect X-rays generated by the X-ray tube. The supporting mechanism supports the X-ray tube and the X-ray detector. The reconstruction circuitry is configured to reconstruct image data based on output data of the X-ray detector. The inverter high voltage generator includes a DC power supply, an inverter, a high voltage converter, a discharge detector, a controller. The DC power supply is configured to generate a direct current. The inverter is configured to convert the direct current from the DC power supply to an alternating current by switching. The high voltage converter is configured to convert an AC output pulse from the inverter to a high voltage to be applied to the X-ray tube. The discharge detector is configured to detect an electric discharge that has occurred in the X-ray tube. The controller is configured to control, upon detection of the discharge, switching of the inverter to change a pulse width or a frequency of the AC output pulse from the inverter so as to gradually increase a measured tube voltage value of the X-ray tube up to a target tube voltage value.

In the following, an X-ray computed tomography apparatus 1 and an X-ray generation apparatus 25 according to the present embodiment will be described in detail with reference to the drawings.

FIG. 1 shows a configuration of the X-ray computed tomography apparatus according to the present embodiment. As shown in FIG. 1, the X-ray computed tomography apparatus 1 includes a gantry 10 and a console 30.

The gantry 10 includes a rotating frame 11 within a housing (not shown in the drawings) in which a bore is provided. The rotating frame 11 is housed in the housing so that a central axis Z of the housing is coincident with a central axis (rotation axis) Z of the rotating frame 11. The rotating frame 11 includes an X-ray tube 13 and an X-ray detector 15 opposed to each other. The rotating frame 11 supports the X-ray tube 13 and X-ray detector 15 to be rotatable about the rotation axis Z. A FOV (Field of View) is set in the bore of the rotating frame 11 or the housing. A top 17 is arranged so that an imaging region of a subject (patient) P is included within the FOV. The rotating frame 11 is connected to a rotation motor 19. The rotation motor 19 rotates the rotating frame 11 at a constant angular speed in accordance with control by the gantry control circuitry 21 to rotate the X-ray tube 13 and the X-ray detector 15 around the rotation axis Z.

The X-ray tube 13 generates X-rays by receiving a high voltage from the inverter high voltage generator 23. The inverter high voltage generator 23 applies a high voltage to the X-ray tube 13 in accordance with control by the gantry control circuitry 21. The inverter high voltage generator 23 has a function of detecting a discharge occurring in the X-ray tube 13. Upon detection of a discharge, the inverter high voltage generator 23 does not abruptly increase the tube voltage to a predetermined voltage, but instead gradually increases the tube voltage in accordance with a change over time, in order to prevent inducing further discharge. The X-ray tube 13 and the inverter high voltage generator 23 form an X-ray generation apparatus 25. The operation of the X-ray generation apparatus 25 will be explained later in detail.

The X-ray detector 15 detects X-rays generated by the X-ray tube 13. The X-ray detector 15 includes a plurality of X-ray detection elements arranged two-dimensionally. For example, the plurality of X-ray detection elements are arranged along an arc centered around the rotation axis Z of the rotating frame 11. The direction of arranging the X-ray detection elements along the arc is called a channel direction. The plurality of X-ray detection elements arranged in the channel direction are called an X-ray detection element array. A plurality of X-ray detection element arrays are arranged in a direction along the rotation axis Z. Each of the X-ray detection elements detects X-rays generated by the X-ray tube 13, and generates an electrical signal (current signal) in accordance with the intensity of the detected X-rays. The generated electrical signal is supplied to a data acquisition system (DAS) 27.

The data acquisition system 27 acquires electrical signals for respective views via the X-ray detector 15 in accordance with control by the gantry control circuitry 21. As is well known, a view corresponds to a rotation angle of the rotating frame 11 about the rotation axis Z. In terms of signal processing, a view corresponds to a sampling point of data when the rotating frame 11 rotates. The data acquisition system 27 converts the acquired analog electrical signals into digital data. The digital data is called raw data. A non-contact transmitter 29 supplies the raw data to the console 30 for each predetermined view.

The gantry control circuitry 21 integrally controls each device loaded in the gantry 10, in accordance with an instruction from a system control circuitry 43 in the console 30. For example, the gantry control circuitry 21 controls the rotation motor 19, the inverter high voltage generator 23, and the data acquisition system 27.

The console 30 includes a preprocessor 31, a correction circuitry 33, a reconstruction circuitry 35, a display 37, an operation device 39, a storage 41, and a system control circuitry 43. The preprocessor 31 performs preprocessing including logarithmic transformation and sensitivity correction for the raw data transmitted from the transmitter 29. The preprocessed data is called projection data. The correction circuitry 33 corrects projection data in a view section containing a view in which a discharge is detected, based on at least one of projection data in a view section temporally preceding the view section in which a discharge is detected and projection data in a view section temporally subsequent to the view section in which a discharge is detected. The reconstruction circuitry 35 reconstructs image data concerning a subject P based on the projection data. The display 37 displays the image data generated by the reconstruction circuitry 35. The operation device 39 accepts various instructions and information inputs from a user via an input device. The storage 41 stores the raw data, projection data, and image data. The storage 41 also stores a control program. The system control circuitry 43 reads the control program stored in the storage 41, expands it in a memory, and controls the respective units in accordance with the expanded control program.

In the following, the X-ray computed tomography apparatus 1 according to the present embodiment will be described in detail.

FIG. 2 shows the configuration of the X ray generation apparatus 25 according to the present embodiment. As shown in FIG. 2, the X-ray generation apparatus 25 includes the X-ray tube 13 and the inverter high voltage generator 23. The inverter high voltage generator 23 includes a DC power supply 51, an inverter 53, a high voltage converter 55, a tube voltage detector 57, a tube current detector 59, a discharge detector 61, a switching controller 63, and a gate circuitry 65. The inverter high voltage generator 23 according to the present embodiment is applicable to both a square-wave type (non-resonant type) and a resonant type.

The DC power supply 51 generates a direct current based on an alternating current supplied from power supply equipment provided in an examination room, for example, in which the gantry 10 is placed. Specifically, the DC power supply 51 includes a rectifier circuit and a smoothing capacitor. The rectifier circuit rectifies an alternating current supplied from the power supply equipment to a direct current. The smoothing capacitor smooths the alternating current rectified by the rectifier circuit. The alternating current is converted to a direct current by a rectifying and smoothing process. The power supply equipment that supplies power to the DC power supply 51 is not limited to the power supply equipment, and may include a capacitor or a rechargeable battery.

The inverter 53 converts a direct current from the DC power supply 51 into an AC output pulse by switching. The inverter 53 has a plurality of switches between the DC power supply 51 and the high voltage converter 55. The inverter 53 converts a direct current into an AC output pulse by selectively switching the plurality of switches at the timing according to control by the switching controller 63. If the inverter high voltage generator 23 is a square-wave type, the inverter 53 selectively switches the plurality of switches to convert a direct current from the DC power supply 51 into an AC voltage pulse and an AC current pulse each having a square-wave. If the inverter high voltage generator 23 is a resonant type, the inverter 53 selectively switches the plurality of switches to convert a direct current from the DC power supply 51 into a square-wave AC voltage pulse and a sine wave AC current, or a sine wave AC voltage and a square-wave AC current pulse. The cycle and pulse width of the output pulse from the inverter 53 are determined in accordance with the switching cycle of each switch. The speed of the change over time of tube voltage is adjusted by the pulse width and cycle of the output pulse.

The high voltage converter 55 converts the AC output pulse from the inverter 53 into a DC high voltage. Specifically, the high voltage converter 55 includes a high voltage transformer and a high voltage rectifier. The high voltage transformer boosts the output voltage (primary voltage) from the inverter 53 to an AC high voltage (secondary voltage) through an insulated magnetic circuit. The high voltage rectifier rectifies the AC high voltage boosted by the high voltage transformer into a DC high voltage. The AC high voltage is converted to a DC high voltage by the boosting or rectifying.

The X-ray tube 13 is connected to the high voltage converter 55 through an anode side cable and a cathode side cable. The X-ray tube 13 includes a cathode 133 and an anode 135 within a case 131. The high voltage converter 55 and the anode 135 are connected to the anode side cable, and the high voltage converter 55 and the cathode 133 are connected to the cathode side cable. The case 131 is maintained under vacuum. The cathode 133 includes a filament 137. The filament 137 is heated by receiving a filament current from a filament heating transformer not shown in the drawings. The heated filament 137 emits thermoelectrons. The anode 135 includes a target 139 that rotates around the rotation axis R. A high voltage is applied between the cathode 133 and anode 135 from the high voltage converter 55 through the anode side cable and cathode side cable. The thermoelectrons emitted from the filament 137 collide into the target 139 due to the functioning of an electric field produced by the high voltage. An X-ray beam is generated by interaction between the thermoelectrons and the target 139. The thermoelectrons flow from the anode 135 to the anode side cable after colliding into the target 139.

The tube voltage detector 57 is connected between the X-ray tube 13 and the high voltage converter 55. The tube voltage detector 57 detects the high voltage applied between the cathode 133 and the anode 135 as a tube voltage. A detected tube voltage value is provided to the discharge detector 61 and the switching controller 63.

The tube current detector 59 is connected to the anode side cable. The tube current detector 59 detects as a tube current a current flowing through the anode side cable resulting from the thermoelectrons flowing from the cathode 133 to the anode 135. The detected tube current value is provided to the discharge detector 61.

The discharge detector 61 detects an electrical discharge in the X-ray tube 13 based on the change over time in tube voltage or tube current value. An electrical discharge is the phenomenon where an abnormal current flows between the cathode 133 and the anode 135 when the vacuum level in the case 131 is degraded due to an insulation break down in the case 131. When an electrical discharge occurs, the tube current abruptly increases, and the tube voltage abruptly decreases. The discharge detector 61 detects an electrical discharge by using the change over time in the X-ray tube output value which is unique to the time when an electrical discharge occurs. If an electrical discharge is detected, the discharge detector 61 switches a discharge flag from OFF to ON. The discharge flag is transferred to the switching controller 63.

The switching controller 63 controls switching by the inverter 53. The switching controller 63 changes a method for controlling switching in the inverter 53 between the ON state (discharge period) and the OFF state (non-discharge period) of the discharge flag. In the non-discharge period, the switching controller 63 executes a normal feedback control. That is, in the non-discharge period, the switching controller 63 executes a normal feedback control by using the tube voltage value and the set tube voltage value to maintain the tube voltage at the set voltage value. The set tube voltage value is a tube voltage value set as an X-ray condition, and is to be requested when collecting raw data used for reconstruction of an image. In the discharge period, the switching controller 63 controls switching of the inverter 53 so that the tube voltage value slowly increases up to the set tube voltage value as time passes.

As shown in FIG. 2, the switching controller 63 includes a threshold setting circuitry 631, a tube voltage control level determination circuitry 633, and a switch driver 635.

The threshold setting circuitry 631 sets a threshold used at the tube voltage control level determination circuitry 633. The threshold setting circuitry 631 changes a method for setting a threshold between the non-discharge period and the discharge period. In the non-discharge period, the threshold setting circuitry 631 sets the set tube voltage value as a threshold. In the discharge period, the threshold setting circuitry 631 sets as time passes one of multiple provisional values as a threshold from a smallest value, so that the tube voltage value gradually becomes closer to the set tube voltage value as time passes. The threshold may be increased continuously or stage-by-stage as time passes.

The tube voltage control level determination circuitry 633 determines a tube voltage control level based on the tube voltage value received from the tube voltage detector 57, and the threshold received from the threshold setting circuitry 631. Specifically, the tube voltage control level determination circuitry 633 first compares the tube voltage value with the threshold. The tube voltage control level determination circuitry 633 then determines a tube voltage control level in accordance with the deviation between the tube voltage value and the threshold.

The switch driver 635 switches multiple switches in the inverter 53 independently at a switching timing in accordance with the tube voltage control level determined by the tube voltage control level determination circuitry 633.

As shown in FIG. 2, the gate circuitry 65 is connected to the switch driver 635 of the switching controller 63. The gate circuitry 65 switches between activating and inactivating of the switch driver 635. Specifically, the gate circuitry 65 supplies a gate pulse to the switch driver 635 in response to an initiation instruction from the gantry control circuitry 21 to drive the switch driver 635. Upon the application of the gate pulse, the switch driver 635 switches multiple switches, as explained above. The gate circuitry 65 supplies a stop signal to the switch driver 635 in response to a termination instruction from the gantry control circuitry 21 to stop driving of the switch driver 635. The stop signal is supplied at the time of completion of the scanning sequence. Upon the reception of the stop signal, the switch driver 635 stops switching of multiple switches. By this action, the operation of the inverter high voltage generator 23 is stopped, namely, application of the tube voltage is stopped, and X-ray generation is then stopped.

Next, an example of the operation of the X-ray generation apparatus 25 when executing CT scanning, focused mainly on the operation of the switching controller 63, will be explained. The switching control according to the embodiment includes a pulse width modulation system and a frequency modulation system. The pulse width modulation system is a system to change a tube voltage value by changing the pulse width of an output pulse of the inverter 53 as time passes. The frequency modulation system is a system to change a tube voltage value by changing the frequency of an output pulse of the inverter 53 in accordance with time. The cases where the pulse width modulation system is applied, and the frequency modulation system is applied will be explained below. In the following, the discharge detector 61 is assumed to detect a discharge using a tube voltage value.

Figure 3:
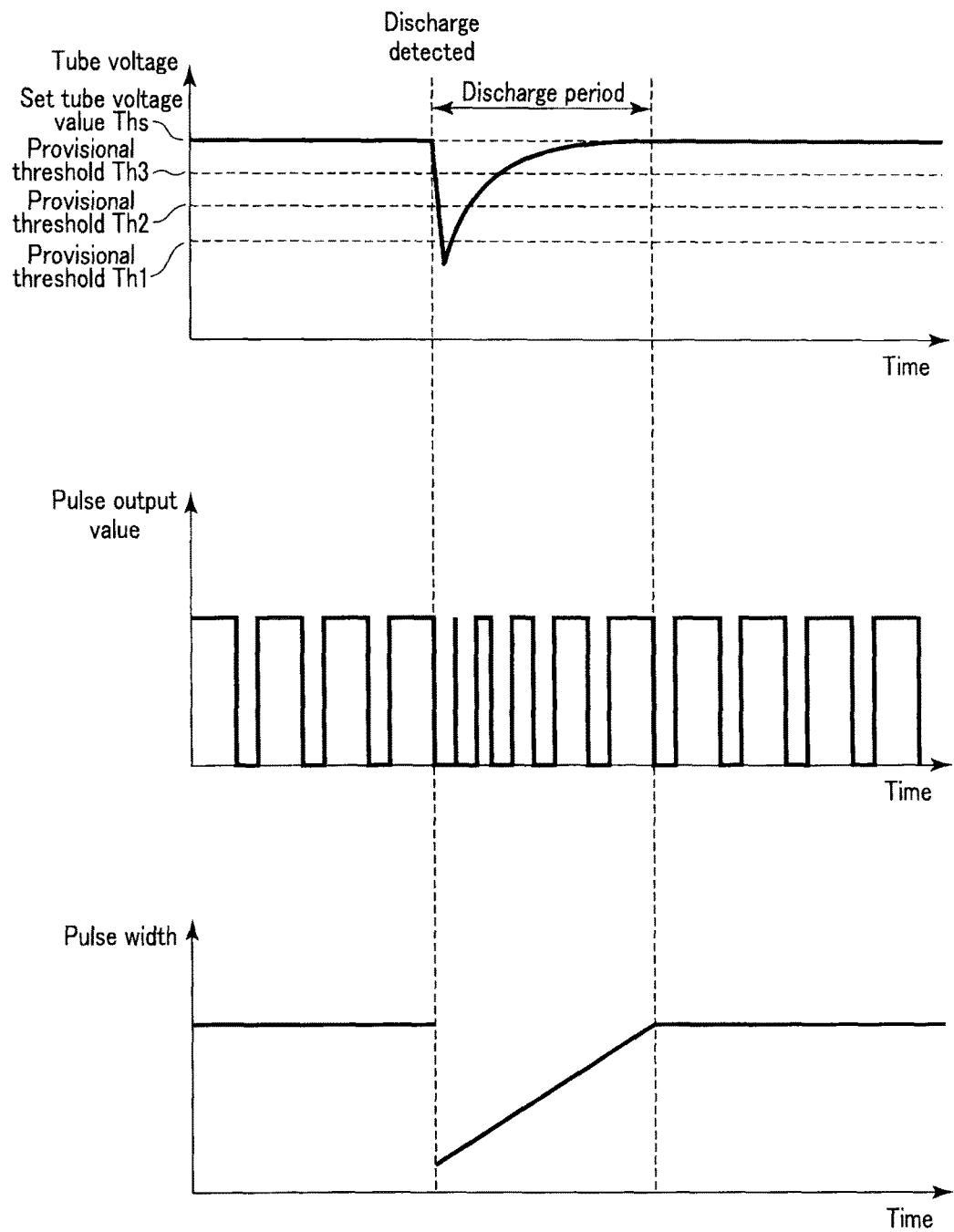
FIG. 3 illustrates an example timing chart of an operation of a pulse width modulation system performed by the X-ray generation apparatus shown in FIG. 2.

FIG. 3 is an example timing chart of the operation of a pulse width modulation system performed by the X-ray generation apparatus 25. The upper graph in FIG. 3 shows a change in the tube voltage value, the middle graph in FIG. 3 shows changes over time in the output pulse from the inverter 53, and the lower graph in FIG. 3 shows the pulse width of the output pulse from the inverter 53. In the upper graph in FIG. 3, the vertical axis represents the tube voltage value, and the horizontal axis represents time. In the middle graph in FIG. 3, the vertical axis represents the output pulse value, and the horizontal axis represents time. In the lower graph in FIG. 3, the vertical axis represents the pulse width of the output pulse, and the horizontal axis represents time.

During CT scanning, the discharge detector 61 monitors the time differential value of the tube voltage value obtained from the tube voltage detector 57, and repeatedly determines whether the time differential value exceeds a threshold for discharge detection (hereinafter referred to as "discharge detection threshold"). If the discharge detector 61 determines that the time differential value of the tube voltage value does not exceed the discharge detection threshold, the discharge flag is set to be OFF. The discharge detection threshold can be freely set through the operation device 39. In the non-discharge period in which the discharge flag is OFF, the threshold setting circuitry 631 sets the set tube voltage value Ths as a threshold. The tube voltage control level determination circuitry 633 determines a tube voltage control level by comparing the tube voltage value received from the tube voltage detector 57 and the set tube voltage value Ths. The switch driver 635 switches multiple switches in the inverter 53 independently at a switching timing in accordance with the determined tube voltage control level, and the inverter 53 outputs a pulse having the pulse width matching the tube voltage control level. The high voltage matching the output pulse is applied between the cathode 133 and the anode 135. By the above operation, the tube voltage value is maintained at the set tube voltage value Ths.

If a discharge occurs within the case 131 of the X-ray tube 13, the tube voltage abruptly decreases, and the time differential value of the tube voltage value abruptly increases. If the discharge detector 61 determines that the time differential value of the tube voltage value exceeds the discharge detection threshold, the discharge flag is set to ON. In the discharge period in which the discharge flag is ON, the threshold setting circuitry 631 sets a threshold by sequentially selecting the smallest value from among a plurality of provisional thresholds.

Specifically, if a discharge is detected, the threshold setting circuitry 631 immediately sets the smallest provisional threshold Th1 as a threshold. The tube voltage control level determination circuitry 633 determines a tube voltage control level by comparing the tube voltage value received from the tube voltage detector 57 and the smallest provisional threshold Th1. The switch driver 635 switches multiple switches in the inverter 53 independently at a switching timing in accordance with the determined tube voltage control level, and the inverter 53 repeatedly outputs a pulse having the pulse width matching the tube voltage control level. The high voltage matching the output pulse is applied between the cathode 133 and the anode 135. By the above operation, the tube voltage value increases toward the first provisional threshold Th1.

If a predetermined condition is satisfied, the threshold setting circuitry 631 sets a second smallest provisional threshold Th2 as a threshold. The predetermined condition may be a predetermined elapsed time, or an increase of the tube voltage value to the threshold. The tube voltage control level determination circuitry 633 determines a tube voltage control level by comparing the tube voltage value received from the tube voltage detector 57 and the second provisional threshold Th2. The switch driver 635 switches multiple switches in the inverter 53 independently at a switching timing in accordance with the determined tube voltage control level, and the inverter 53 repeatedly outputs a pulse having the pulse width matching the tube voltage control level. The high voltage matching the output pulse is applied between the cathode 133 and the anode 135. By the above operation, the tube voltage value increases toward the second provisional threshold Th2.

Every time the predetermined condition is satisfied, the threshold setting circuitry 631 sets the next smallest provisional threshold th as a threshold. Afterwards, the tube voltage control level for the newly set provisional threshold is determined, and the switches in the inverter 53 are switched at a timing matching the determined tube voltage control level in a similar manner.

During the discharge period, the discharge detector 61 monitors the tube voltage value obtained from the tube voltage detector 57, and repeatedly determines whether the tube voltage value reaches a threshold for canceling the discharge period (hereinafter referred to as "discharge period cancellation threshold"). If the discharge detector 61 determines that the tube voltage value does not reach the discharge period cancellation threshold, the discharge flag is set to ON. If the discharge detector 61 determines that the tube voltage value reaches the discharge period cancellation threshold, the discharge flag is set to OFF. By the above operation, the discharge period is canceled, and is transferred to the non-discharge period.

As explained above, in the pulse width modulation system, the switching controller 63 gradually increases the threshold for feedback control as time passes, and the pulse width of the output pulse of the inverter 53 is gradually increased. Accordingly, the tube voltage value abruptly decreased due to a discharge can be increased to the set tube voltage value.

An example of the operation of the X-ray generation apparatus 25 when applying the frequency modulation system will be explained. The explanation of operations similar to the case where the pulse width modulation system is applied will be omitted.

FIG. 4 is an example timing chart of the operation of a frequency modulation system performed by the X-ray generation apparatus 25. The upper graph in FIG. 4 shows a change in the tube voltage value, the middle graph in FIG. 4 shows a change over time in the output pulse from the inverter 53 and the lower graph in FIG. 4 shows the frequency of the output pulse from the inverter 53. In the upper graph in FIG. 4, the vertical axis represents the tube voltage value, and the horizontal axis represents time. In the middle graph in FIG. 4, the vertical axis represents the output pulse value, and the horizontal axis represents time. In the lower graph in FIG. 4, the vertical axis represents the frequency of the output pulse, and the horizontal axis represents time.

As shown in FIG. 4, if a discharge is detected, the threshold setting circuitry 631 immediately sets the smallest provisional threshold Th1 as a threshold. The tube voltage control level determination circuitry 633 determines a tube voltage control level by comparing the tube voltage value received from the tube voltage detector 57 and the smallest provisional threshold Th1. The switch driver 635 switches multiple switches in the inverter 53 independently at a switching timing in accordance with the determined tube voltage control level, and the inverter 53 repeatedly outputs a pulse having the frequency matching the tube voltage control level. The high voltage matching the output pulse is applied between the cathode 133 and the anode 135. By the above operation, the tube voltage value increases toward the first provisional threshold Th1.

If a predetermined condition is satisfied, the threshold setting circuitry 631 sets a second smallest provisional threshold Th2 as a threshold. The predetermined condition may be a predetermined time elapsed, or an increase of the tube voltage value to the threshold. The tube voltage control level determination circuitry 633 determines a tube voltage control level by comparing the tube voltage value received from the tube voltage detector 57 and the second provisional threshold Th2. The switch driver 635 switches multiple switches in the inverter 53 independently at a switching timing in accordance with the determined tube voltage control level, and the inverter 53 repeatedly outputs a pulse having the frequency matching the tube voltage control level. The high voltage matching the output pulse is applied between the cathode 133 and the anode 135. By the above operation, the tube voltage value increases toward the second provisional threshold Th2.

As explained above, in the frequency modulation system, the switching controller 63 gradually increases the threshold for feedback control as time passes, and the frequency of the output pulse of the inverter 53 is gradually increased. Accordingly, the tube voltage value abruptly decreased due to a discharge can be increased to the set tube voltage value.

In the present embodiment, the gate circuitry 65 allows the switch driver 635 to continuously switch multiple switches even when the discharge detector 61 detects a discharge. Thus, the inverter high voltage generator 23 according to the present embodiment continues operating even when a discharge is detected.

Figure 5:
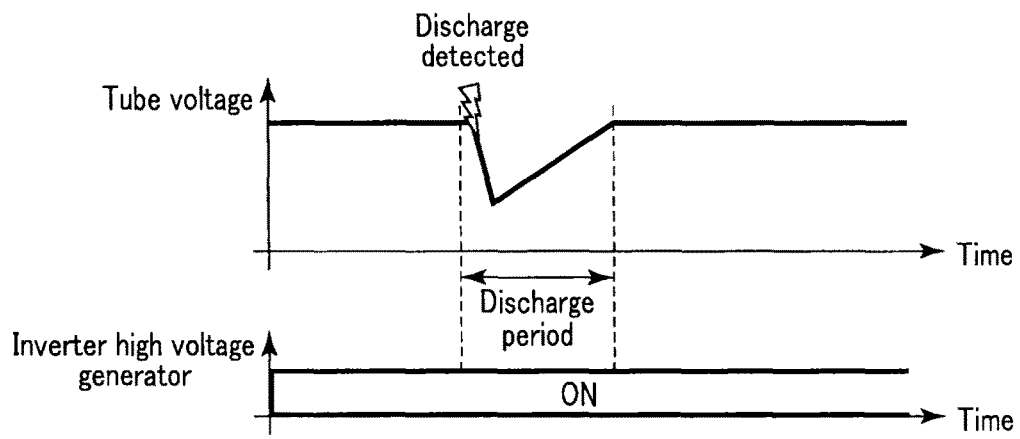
FIG. 5 illustrates a timing chart of an operation of an inverter high voltage generator shown in FIG. 1 along with a change over time in a tube voltage.
Figure 7:
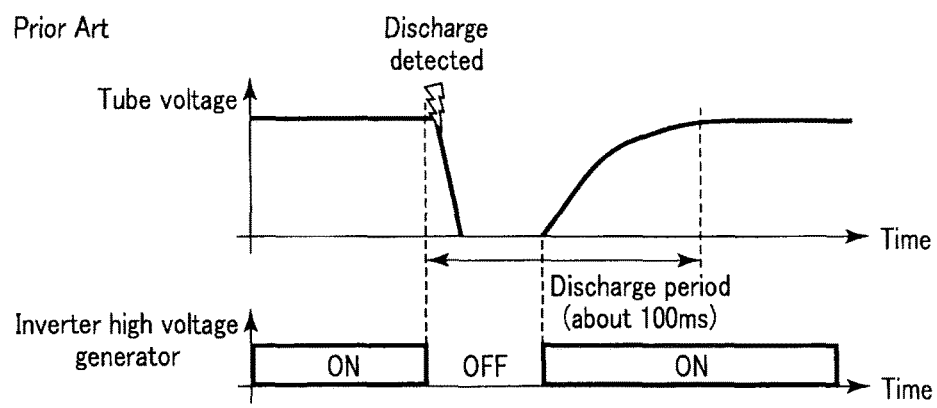
FIG. 7 illustrates a timing chart of an operation of the conventional inverter high voltage generator along with the change over time in the tube voltage.
Figure 8:
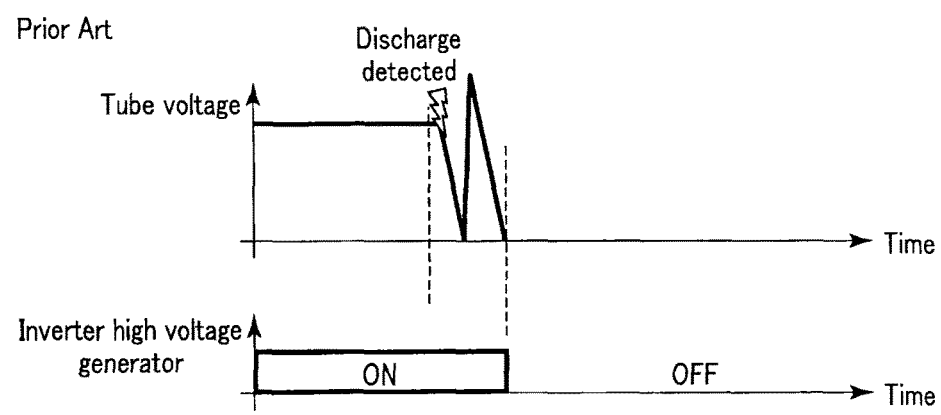
FIG. 8 illustrates a timing chart of another operation of the conventional inverter high voltage generator along with the change over time in the tube voltage.

The operation sequence of the inverter high voltage generator between the present embodiment and the conventional example will be compared with reference to FIGS. 5 and 7. FIG. 5 is the timing chart showing the operation of the inverter high voltage generator 23 according to the present embodiment along with a change over time in tube voltage, and FIG. 7 is the timing chart showing the operation of the conventional inverter high voltage generator along with a change over time in tube voltage. In a conventional generator, it is assumed that the pulse width or frequency is not modulated before and after the occurrence of a discharge. As shown in FIG. 7, the conventional inverter high voltage generator stops operation until the atmosphere within the X-ray tube becomes stable if a discharge is detected. That is, the gate circuitry controls the switch driver to stop the switching operation. Accordingly, as shown in FIG. 7, the recovery time from the time when a discharge occurs to the time when the tube voltage reaches a target tube voltage value (time length of discharge period) is about 100 ms. In addition, as shown in FIG. 8, if the pulse width corresponding to the target tube voltage value is maintained under the case where a discharge is detected, a discharge may be induced due to an abrupt increase of tube voltage value due to the discharge, or the inverter high voltage generator may be damaged.

However, as shown in FIG. 5, the inverter high voltage generator 23 according to this embodiment controls the pulse width or frequency upon detection of a discharge so that the tube voltage value gradually increases up to the target tube voltage value. In this situation, the inverter high voltage generator 23 according to the embodiment continues operating even when a discharge is detected. That is, the gate circuitry 65 does not control the switch driver 635 to stop switching operation, namely, the switch driver 635 continues switching multiple switches. Accordingly, the inverter high voltage generator 23 according to the embodiment achieves recovery from a discharge in a short period of time in comparison with the conventional inverter high voltage generator.

Projection data collected while the tube voltage value is lower than the set tube voltage value due to a discharge generates artifacts in a reconstructed image. The period when discharge is occurring is relatively short, such as several milliseconds. The correction circuitry 33 according to the embodiment corrects projection data collected while the tube voltage value is lower than the set tube voltage value so as to be usable for reconstruction of an image.

Figure 6:
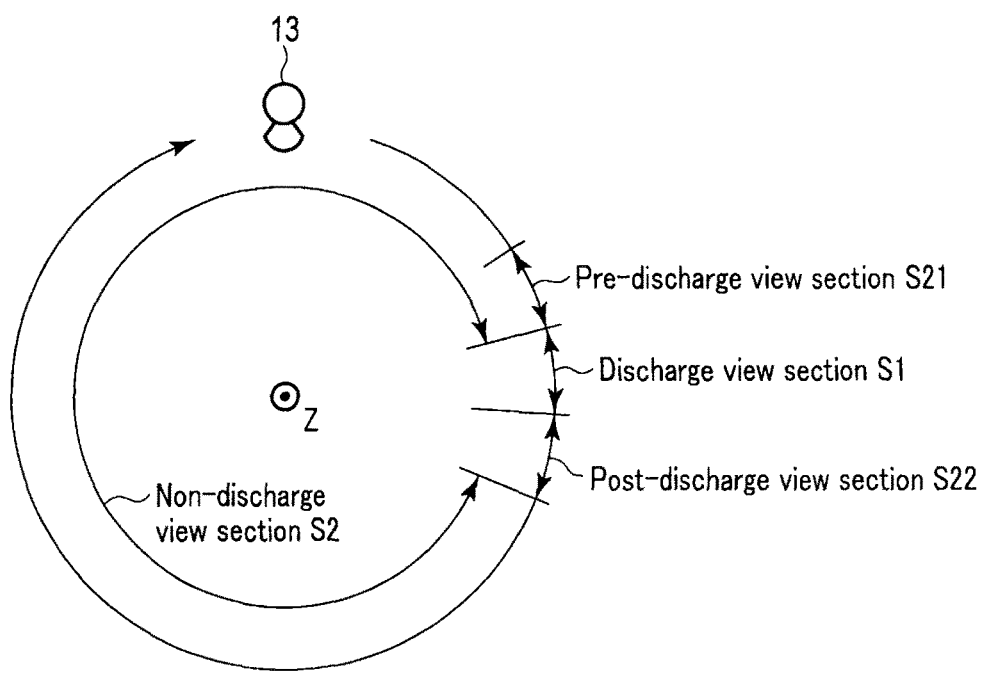
FIG. 6 illustrates correction processing of projection data at a correction circuitry shown in FIG. 1.

FIG. 6 illustrates correction processing of projection data at the correction circuitry 33. As shown in FIG. 6, the X-ray tube 13 radiates X-rays while rotating around the rotation axis Z along with rotation of the rotating frame during CT scanning. A view section in the discharge period is called a discharge view section S1, and a view section in the non-discharge period is called a non-discharge view section S2. The discharge view section S1 includes a view at the time when a discharge is detected. Projection data in the discharge view section S1 is based on raw data collected in the state where the tube voltage value is lower than the set tube voltage value. Accordingly, the projection data in the discharge view section S1 cannot be used as-is for image reconstruction. The projection data in the discharge view section S1 is to be corrected by the correction circuitry 33.

The correction circuitry 33 corrects projection data in the discharge view section S1 based on projection data in a view section S21 (hereinafter referred to as "pre-discharge view section") that is in the non-discharge view section S2 and temporally precedes the discharge view section S1, and based on projection data in a view section S22 (hereinafter referred to as "post-discharge view section") that is temporally subsequent to the discharge view section S1. That is, the correction circuitry 33 corrects projection data in the discharge view section S1 based on at least one of projection data in the pre-discharge view section S21 and projection data in the post-discharge view section S22. For example, the pre-discharge view section S21 and the post-discharge view section S22 may be automatically set by the correction circuitry 33, or freely set by a user through the operation device 39. Each of the pre-discharge view section S21 and the post-discharge view section S22 may include a single view, not a plurality of views.

For the scanning method in which the X-ray tube 13 does not rotate multiple times, the pre-discharge view section and the post-discharge view section are automatically set to view sections adjacent to the discharge view section. If an X-ray path, which is identical to a certain X-ray path of projection data in the discharge view section, is present in the non-discharge view section, the projection data of the certain X-ray path in the discharge view section may be replaced with projection data of the X-ray path in the non-discharge view section.

For the scanning method in which the X-ray tube 13 rotates multiple times, the pre-discharge view section and the post-discharge view section may be set to a view section corresponding to the discharge view section, or a view section 180° different from the discharge view section. If a top 17 is stationary, the correction circuitry 33 may replace the projection data in the discharge view section with projection data in the pre-discharge view section, or projection data in the post-discharge view section.

After completion of correction processing, the reconstruction circuitry 35 reconstructs an image based on the corrected projection data in the discharge view section, and the projection data in the non-discharge view section. By this processing, the artifact component that is included in a reconstructed image due to a discharge decreases in comparison with the case where correction processing is not performed by the correction circuitry 33.

In image reconstruction, it is not necessary to use projection data in the discharge view section. The reconstruction circuitry 35 may reconstruct an image based on the projection data in the non-discharge view section. As stated above, the inverter high voltage generator 23 according to the embodiment achieves a reduction of recovery time from the occurrence of a discharge in comparison with the conventional generator. Therefore, an image reconstructed without using projection data in the discharge view section according to the embodiment includes less artifact components due to a discharge in comparison with the image reconstructed by the conventional method. The user can freely set whether or not to use projection data in the discharge view section through the operation device 39.

In addition, the switching controller 63 according to the embodiment may change the time required to recover from a discharge in accordance with the scanning mode. For example, in the scanning mode that requires high time resolution such as cardiac scanning, the gantry control circuitry 21 does not supply a stop instruction to the gate circuitry 65 in order to maintain the operation of the switching controller 63 even if a discharge is detected. In this case, the switching controller 63 reduces the time required to recover from a discharge in comparison with the conventional method. Accordingly, the switching controller 63 controls modification of the pulse width or frequency of the output pulse of the inverter 53 upon detection of a discharge so that the measured tube voltage value gradually increases to the target tube voltage value.

In the scanning mode that does not require high time resolution such as cranial scanning, the gantry control circuitry 21 immediately supplies a stop instruction to the gate circuitry 65 upon detection of discharge. The gate circuitry 65 temporarily stops the switching controller 63 upon reception of the stop instruction. The predetermined stop period may be a time period until the atmosphere within the X-ray tube 13 becomes stable. However, the stop period is not limited as above, but may be freely set through the operation device 39. After the stop period has elapsed, the gantry control circuitry 21 immediately supplies a start instruction to the gate circuitry 65. The gate circuitry 65 supplies a gate pulse to the switch driver 635 upon reception of the start instruction. When the switching controller 63 receives the gate pulse, the switching controller 63 controls modification of the pulse width or frequency of the output pulse of the inverter 53 so that the measured tube voltage value gradually increases up to the target tube voltage value upon detection of a discharge, as explained above.

As explained above, the switching controller 63 according to the embodiment changes the amount of time required to recover from a discharge by changing the time period from when a discharge is detected to when the modulation of pulse width or frequency is controlled, in accordance with the scanning mode.

In the following, the advantageous effects of the present embodiment will be described.

In the conventional technique, when the tube voltage value is abruptly increased to the set tube voltage value after discharge detection, the atmosphere within the X-ray tube is not stable, and a further discharge is likely to be induced. To avoid this, the power supply to the x-ray tube is immediately stopped upon detection of a discharge to temporarily stop X-ray output, and the power supply to the X-ray tube is resumed to output Z-rays after the atmosphere within the X-ray tube becomes stable. In this case, a large amount of artifacts may occur in a reconstructed image because of the large amount of projection data that is not usable for the image reconstruction. In addition, if the tube voltage value is abruptly increased to the set tube voltage value without blocking the power supply to the X-ray tube, further discharge may occur, and the amount of projection data usable for image reconstruction decreases, thereby generating a large amount of artifacts in the reconstructed image.

In contrast to the conventional technique, the X-ray generation apparatus 25 according to the embodiment gradually increases the tube voltage value to the set tube voltage value without stopping power supply to the X-ray tube 13 after the detection of a discharge. Accordingly, the tube voltage value can increase to the set tube voltage value while keeping the atmosphere within the X-ray tube 13 stable. This prevents the induction of further discharges. As a result, in comparison with the conventional technique, the X-ray generation apparatus 25 can rapidly recover the tube voltage value to the set tube voltage value, thereby decreasing the data amount that includes artifacts due to a discharge. Thus, the X-ray generation apparatus 25 reduces artifacts in a reconstructed image in comparison with the conventional technique. In addition, the X-ray computed tomography apparatus according to the embodiment recovers projection data in the discharge view section based on projection data in the non-discharge view section to improve the quality of the reconstructed image.

As stated above, the present embodiment achieves a reduction of image artifacts due to electrical discharges.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
   an X-ray tube configured to generate X-rays;
   an inverter high voltage generator configured to generate a high voltage to be applied to the X-ray tube;
   an X-ray detector configured to detect X-rays generated by the X-ray tube;
   a supporting mechanism that supports the X-ray tube and the X-ray detector; and
   a reconstruction circuitry configured to reconstruct image data based on output data of the X-ray detector,
   wherein the inverter high voltage generator comprises:
   a DC power supply configured to generate a direct current;
   an inverter configured to convert the direct current from the DC power supply to an alternating current by switching;
   a high voltage converter configured to convert the alternating current from the inverter to a high voltage to be applied to the X-ray tube;
   a tube voltage detector configured to detect a measured tube voltage value;
   a discharge detector configured to detect an electrical discharge that has occurred in the X-ray tube; and
   a controller configured to control, upon detection of the electrical discharge, switching of the inverter to change a pulse width or a frequency of the alternating current from the inverter so as to gradually increase the measured tube voltage value of the X-ray tube up to a target tube voltage value.

2. The X-ray computed tomography apparatus according to claim 1, wherein the controller performs feedback control so that the measured tube voltage value of the X-ray tube is immediately adjusted to be equal to the target tube voltage value, when no electrical discharge is detected.

3. The X-ray computed tomography apparatus according to claim 1, wherein the inverter comprises a plurality of switches to convert the direct current from the DC power supply to the alternating current, and the controller changes a switching timing for each of the plurality of switches as time passes upon detection of the electrical discharge so that the measured tube voltage value of the X-ray tube gradually increases up to the target tube voltage value.

4. The X-ray computed tomography apparatus according to claim 1, wherein the inverter comprises a plurality of switches to convert the direct current from the DC power supply to the alternating current,
   wherein the controller further comprises a determination circuitry configured to determine a tube voltage control level in accordance with a deviation between the measured tube voltage value and the target tube voltage value, and a switch driver configured to switch the plurality of switches individually in accordance with the tube voltage control level, wherein the inverter high voltage generator further comprises a gate circuitry configured to switch the switch driver between active and inactive, wherein the switch driver is connected to the gate circuitry that switches the switch driver between active and inactive, and wherein the gate circuitry continues activating the switch driver even if the electrical discharge is detected.

5. The X-ray computed tomography apparatus according to claim 1, further comprising:

a correction circuitry configured to correct output data in a discharge view section which includes a view in which the electrical discharge is detected, based on at least one of output data in a view section temporally preceding the discharge view section and output data in a view section temporally subsequent to the discharge view section.

6. The X-ray computed tomography apparatus according to claim 1, wherein the reconstruction circuitry reconstructs the image data based on output data in a view section other than a discharge view section that includes a view in which the electrical discharge is detected.

7. The X-ray computed tomography apparatus according to claim 1, wherein the controller changes an amount of time required for the measured tube voltage value to recover to the target tube voltage value after the electrical discharge is detected, in accordance with a scanning mode.

8. An X-ray generation apparatus, comprising:

a DC power supply configured to generate a direct current;

an inverter configured to convert the direct current to an alternating current by switching;

a high voltage converter configured to convert the alternating current to a high voltage;

an X-ray tube configured to generate X-rays by receiving the high voltage;

a tube voltage detector configured to detect a measured tube voltage value;

a discharge detector configured to detect an electrical discharge that has occurred in the X-ray tube; and a controller configured to control, upon detection of the electrical discharge, switching of the inverter to change a pulse width or a frequency of the alternating current from the inverter so as to gradually increase the measured tube voltage value of the X-ray tube up to a target tube voltage value.

* * * * *